United States Patent [19]

Nyberg et al.

[11] Patent Number: 5,005,773
[45] Date of Patent: Apr. 9, 1991

[54] SONIC GENERATOR

[75] Inventors: Christopher A. Nyberg, North Vancouver; James G. Jackson, Burnaby; Jan Brdicko, West Vancouver, all of Canada

[73] Assignee: ARC Sonics Inc., Burnaby, Canada

[21] Appl. No.: 332,560

[22] Filed: Mar. 31, 1989

Related U.S. Application Data

[63] Continuation-in-part of Ser. No. 176,716, Apr. 1, 1988, Pat. No. 4,941,134.

[51] Int. Cl.$^5$ ............................................. B01F 11/02
[52] U.S. Cl. ...................................... 241/30; 366/127; 366/600; 241/175
[58] Field of Search ................ 366/108, 127, 600, 114, 366/116, 127, 110; 181/113, 142; 367/142, 148, 156, 168, 174, 175, 176; 310/26, 80, 81, 84, 103–105, 109.111, 112; 166/72; 175/53, 55; 241/1, 30, 170, 184

[56] References Cited

U.S. PATENT DOCUMENTS

| | | | |
|---|---|---|---|
| 2,468,515 | 4/1949 | Robinson | 366/118 |
| 2,960,317 | 11/1960 | Bodine, Jr. | 366/600 |
| 3,153,530 | 10/1964 | Bodine | 366/600 |
| 3,645,458 | 2/1972 | Tobe | 366/110 X |
| 4,728,837 | 3/1989 | Bhadra | 310/8 |
| 4,780,861 | 10/1988 | Stembridge et al. | 367/150 |

*Primary Examiner*—Brian S. Steinberger
*Attorney, Agent, or Firm*—John Russell Uren

[57] ABSTRACT

A sonic generator comprises a resonant bar, a housing and magnetic excitation units connected between the resonant bar and the housing. The magnetic excitation units are connected to the bar at highly stressed points using a mounting connection which is a sleeve having an inside diameter slightly greater than the outside diameter of the bar. A resilient elastomer such as urethane is mounted between the sleeve and the resonant member. The sonic generator may be used for grinding purposes and, in particular, may be used to grind material exceptionally fine with reduced power consumption. The bar is substantially unrestrained so as to allow substantially free vibration.

9 Claims, 6 Drawing Sheets

FIG. 1b MODE SHAPE - 2nd

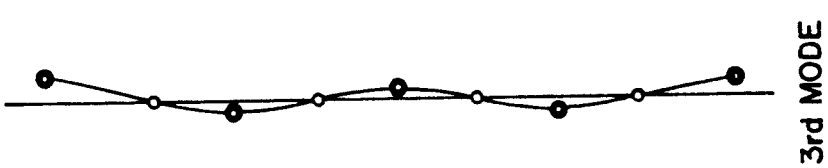
FIG.3d 3rd MODE
FIG.3c 2nd MODE
FIG.3b 1st MODE
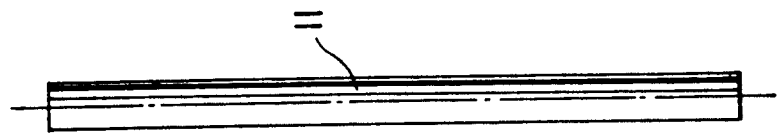
FIG.3a UNDEFLECTED RESONANT MEMBER
○ NODE
● ANTI-NODE

SONIC GENERATOR

CROSS-REFERENCE TO RELATED APPLICATION

This application is a continuation-in-part of co-pending U.S. patent application Ser. No. 176,716, filed Apr. 1, 1988. Now U.S. Pat. No. 4,941,134.

INTRODUCTION

This invention relates to a sonic generator used for the transmission of energy into fluid mediums and, more particularly, to a sonic generator in which the resonant member is substantially unrestrained when vibrating.

BACKGROUND OF THE INVENTION

Sonic generators used to convert electrical energy into acoustic and kinetic energy for transmission to fluid mediums are known. Such devices are illustrated, for example, in U.K. Patent Specification 2,152,728 to Bodine and U.S. Pat. No. 2,468,515 to Robinson.

The sonic generators there disclosed, however, suffer disadvantages. For example, the apparatus taught by Bodine in the aforementioned U. K. patent utilizes resonant drives similar to the types described in Bodine's U.S. Pat. Nos. 3,633,877, 3,684,037, 3,360,056 and 4,265,129. Such drives limit the upper range of frequencies such units can transmit to a fluid medium. Since the transmission of acoustic power between the resonant bar and the fluid is less efficient at lower frequencies, the frequency limitation lowers the acoustic efficiency of the Bodine apparatuses. Bodine also necessarily utilizes a coupling between his orbiting mass oscillators and his resonant bar which attempts to isolate the inertial forces of the vibrating bar from the oscillators. Without such a coupling, the magnitude of the forces generated are sufficient to cause relatively rapid failure of the orbiting mass oscillator drive motors, be they hydraulic or electric.

The above-identified Robinson reference teaches restraining a resonating bar with steel bushings at respectively oppositely located end portions of the bar. Such supports cause energy to be lost through the steel bushing support structure which energy would be better utilized in the fluid medium. This is so since Robinson's method does not allow for free and unrestrained vibration of the resonant member. Rather the resonant member is forced to assume a specific mode shape by the steel retaining bushings. Robinson's structure also imposes a very high stress concentration on the resonant member both at the support point and at the point of maximum bending stress. Such stress concentration can eventually cause unnecessary damage to the resonant member and/or premature failure. It also limits the mechanical stresses that can be sustained by the member without failure.

Existing vibratory grinders generally consist of a rigid housing containing the grinding media such as steel balls mounted on a spring system for support and vibration isolation. The vibration is transmitted through a rotating unbalanced shaft that is rigidly attached to the body of the grinding unit or through an electric motor using an integral unbalanced weight mounted directly to the housing.

The unbalanced shaft embodiment is typically driven by a standard electric motor through a cardan shaft to isolate the motor from the vibration or the eccentric weight which is integral to the electric motor. If the latter, the electric motor vibrates with essentially the same intensity at the grinder itself.

When inducing vibration with an eccentric weight, forces are introduced which must be transmitted from the rotating member through bearings to the body of the grinder. These forces increase with the square of the vibration frequency which practically limits the frequency of the vibration to 30 Hz in commercial scale applications because of the very large force required to vibrate the mass of the grinder unit as the frequency increases. As the rotational frequency increases, the roller bearing becomes limited in load carrying capacity.

When existing vibratory designs are referred to as resonant grinders, it merely means that the vibration frequency corresponds to the natural frequency of the spring-mass system used to isolate the grinder. Resonant operation of such grinders will increase the energy efficiency in the system. However, it is difficult to obtain the necessary vibration amplitude for the grinder with the required spring stiffness for the large grinding masses.

SUMMARY OF THE INVENTION

According to one aspect of the invention, there is provided a sonic generator comprising a resonant member having a plurality of nodes and anti-nodes, resilient housing mounting means located between a housing and said resonant member, said resonant member including a resonant bar and electromagnetic drive means mounted to said resonant bar with drive mounting means, said mounting means comprising an outer sleeve surrounding said resonant bar and a resilient elastomeric material between said outer sleeve and said resonant bar.

According to a further aspect of the invention, there is provided a method of grinding material comprising supporting a member having at least one resonant frequency at nodal points such that said member is substantially unsustained, rigidly mounting at least one grinding chamber on said member at a point other than said nodal points, introducing grinding media into said grinding chamber, electromagnetically exciting said unrestrained member at a resonant frequency of said member, introducing material to be ground into said grinding chamber and removing said material following passage through said grinding media.

According to a further aspect of the invention, there is provided grinding apparatus comprising member having a plurality of nodes and anti-nodes at a resonant frequency, resilient mounting means located between a housing and said member at at least two nodes of said member, electromagnetic drive means mounted to said member at at least one anti-node and at least one grinding chamber mounted to said member close to an anti-node.

BRIEF DESCRIPTION OF THE SEVERAL VIEWS OF THE DRAWINGS

A specific embodiment of the invention will now be described, by way of example only, with the use of drawings in which:

FIG. 1B is a diagrammatic view of the second mode shape of the generator corresponding to FIG. 1A;

FIGS. 3A-3D diagrammatically illustrate the resonant member in its various characteristic mode shapes;

FIG. 6b is a top view of the sonic generator at FIG. 6a.

DESCRIPTION OF SPECIFIC EMBODIMENT

Figure 1A:
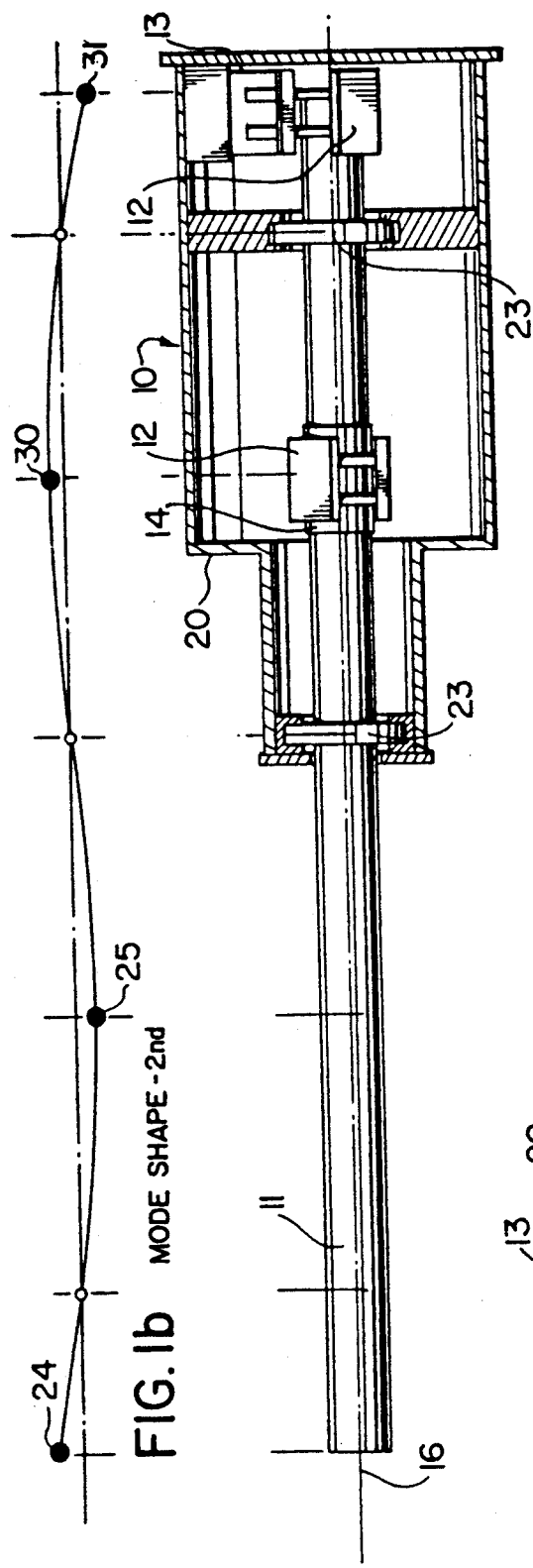
FIG. 1A is a diagrammatic front view of the sonic generator according to the invention.

Referring now to the drawings, a sonic generator is illustrated generally at 10 in FIG. 1A. It comprises a resonant member such as a bar or tube 11 extending substantially the length of the generator 10 and being mounted, at one end, within a housing 20.

Figure 6A:
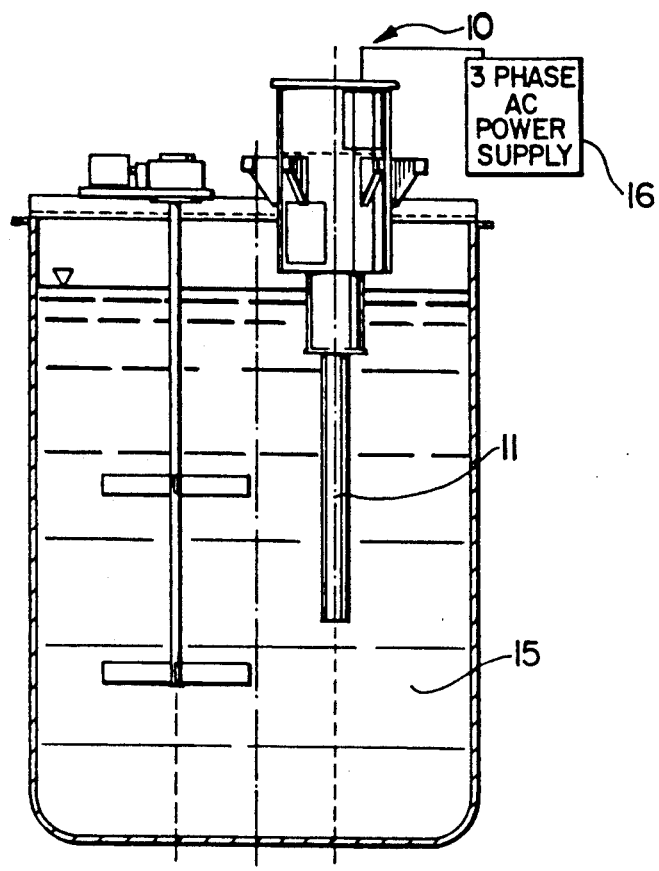
FIG. 6a is a side view illustrating the sonic generator in operating condition in an agitated tank.
Figure 9B:
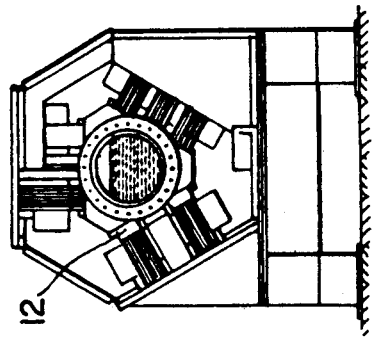
FIG. 9b is an end view taken from the right of FIG. 9A.
Figure 9C:
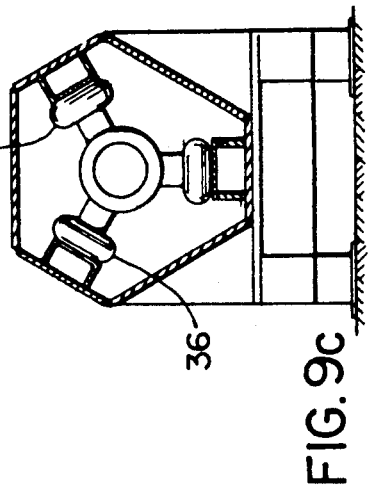
FIG. 9C is an end sectional view taken alon IXB—IXB of FIG. 9A.
Figure 9A:
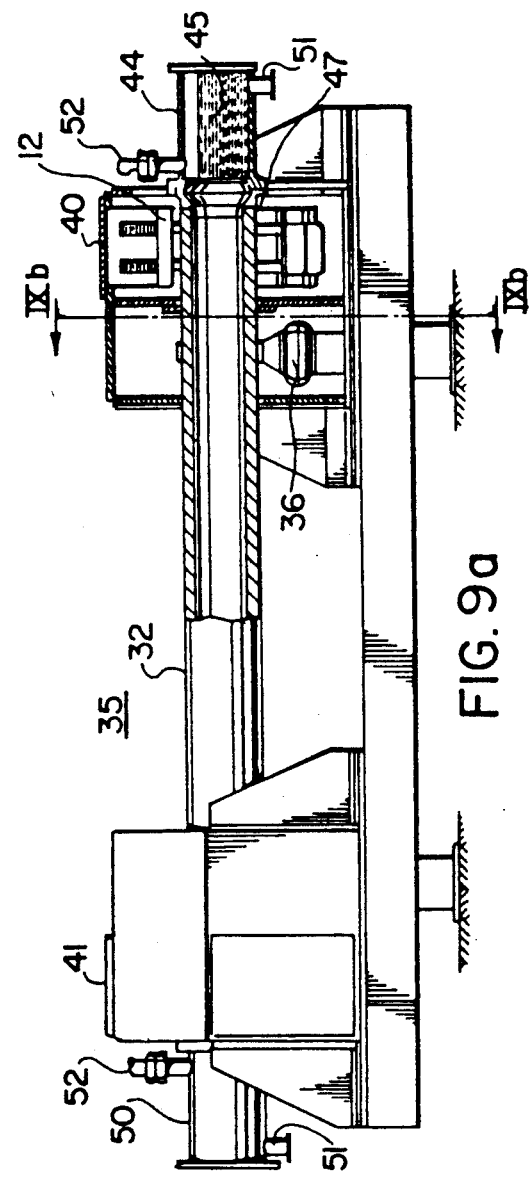
FIG. 9a is a partial sectional side view of the resonant member of FIG. 1 with grinding chambers attached.

Two variable frequency electromagnetic excitation units 13 (only one of which is illustrated in FIG. 9A), each consisting of one electromagnet per phase are energized by a three phase AC power supply 16 (FIG. 6A). The armature components are rigidly mounted using a bolted, clamped or welded connection. They can be directly mounted to the bar if located at a free end or, if located otherwise, to an excitation unit isolation sleeve 14. The sleeve 14 is made from a metal tube, preferably steel, concentrically located about the resonant bar and having an inside diameter 22 slightly greater than the outside diameter of the resonant bar 11 and having a length which is desirably at least as great as its diameter. The annular space between the inside diameter of the isolation sleeve 14 and the outside diameter of the resonant bar 11 is solidly filled with a resilient elastomeric compound 21 such as urethane. The urethane further solidly bonds the sleeve 14 to the bar 11.

OPERATION

Figure 6B:
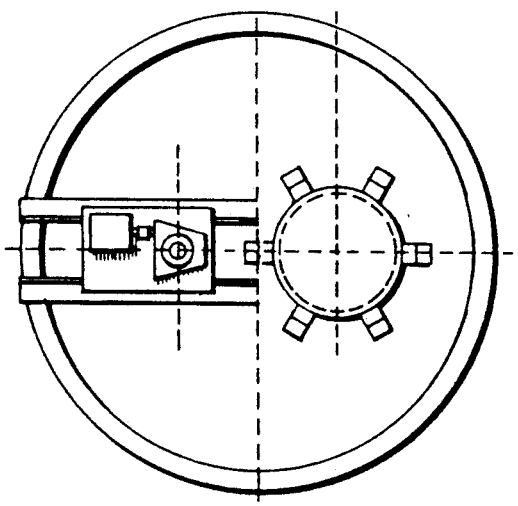

In operation, it will be assumed that the sonic generator 10 is to be mounted in a fluid medium such as illustrated in FIG. 6, such that when the sonic generator 10 is operative, energy is transferred from the resonant bar 11 of the sonic generator 10 to the fluid medium 15.

The mode shape of the resonant member 11 including the isolation sleeves 14 and the armatures 12 is known for the various natural frequencies of the system. For example and with reference to FIG. 3, the undeflected resonant bar 11 is illustrated diagrammatically in FIG. 3A and the three mode shapes for the three lowest natural frequencies of the member 11 are illustrated in FIGS. 3B, 3C and 3D, respectively.

Figure 2:
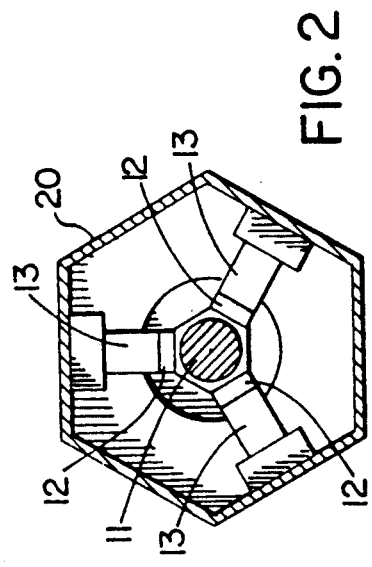
FIG. 2 is an end view of the sonic generator of FIG. 1.
Figure 4:
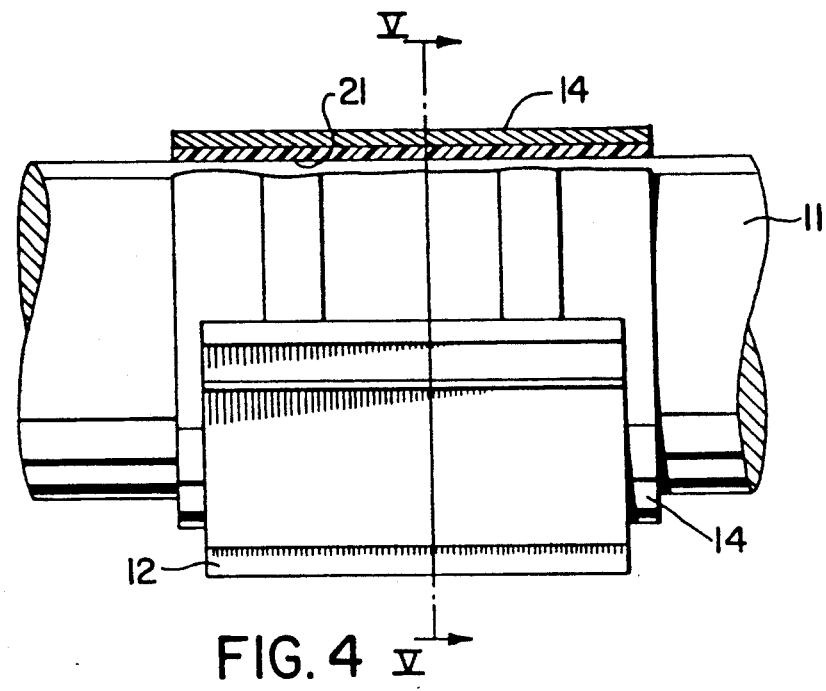
FIG. 4 is an enlarged side view of the motor mounting area of the sonic generator according to the invention.
Figure 5:
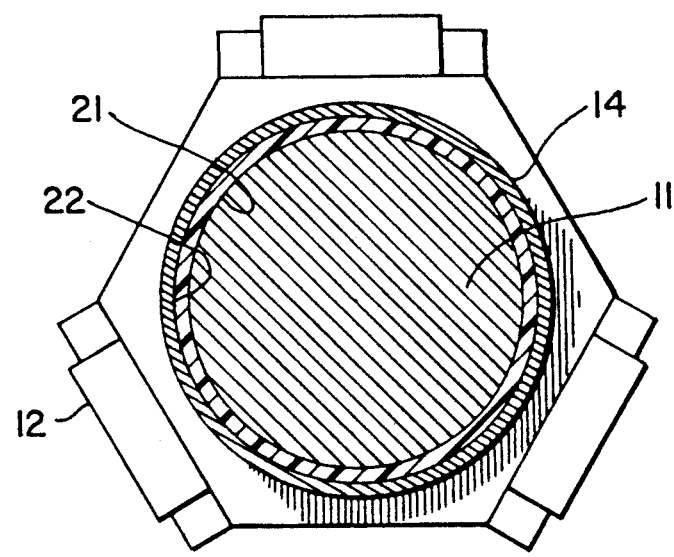
FIG. 5 is an end of the motor mounting area of FIG. 4 taken along the plane V—V of FIG. 4.

To excite the resonant member 11, the magnetic excitation units 13 are energized at the desired natural frequency of the resonant member 11 by a variable frequency three phase AC power supply 16. Each phase of the power supply 16 energizes one of three phases of the magnetic excitation units 13. Each phase of the excitation units 13 is spaced at 120 degrees radially about the resonant member 11 as illustrated in FIG. 2 such that the force vector produced by the excitation unit rotates at a constant rate about the longitudinal axis 16 of the resonant member 11 at the driven frequency. This causes a three dimensional, nutational vibration of the resonant member 11 which allows acoustic energy to propagate radially off of the resonant bar 11 in all directions. When the member 11 is excited at its natural frequency, an increased power transmission ability for a given excitation force is obtained.

Figure 7:
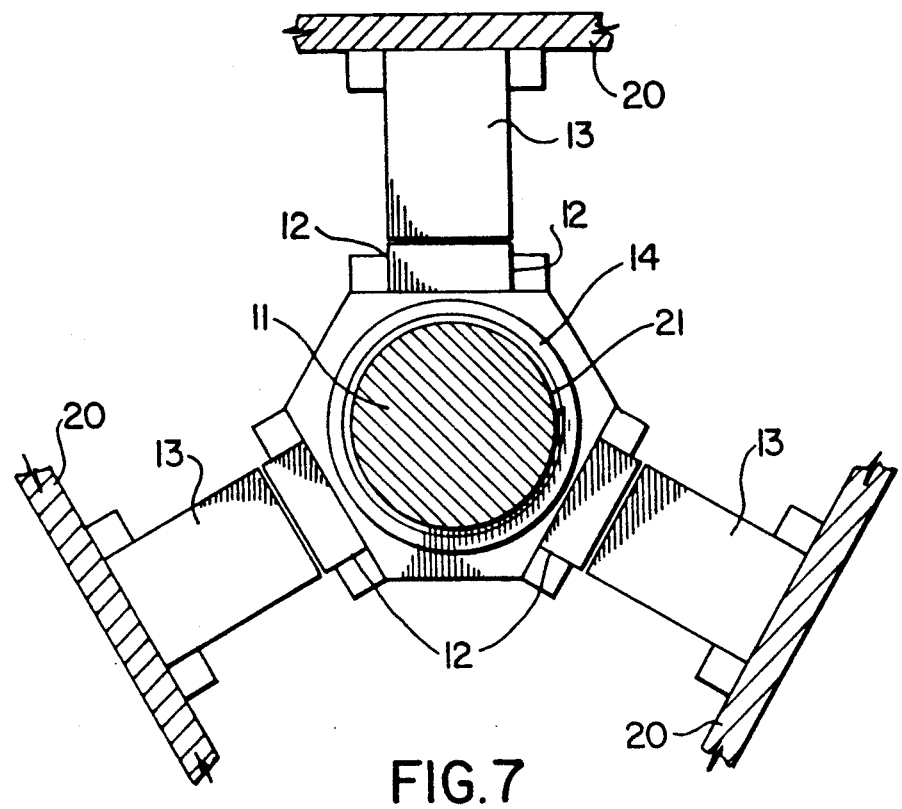
FIG. 7 is an end view of the electromagnetic excitation units and the armatures attached to the bar through the mounting means.
Figure 8:
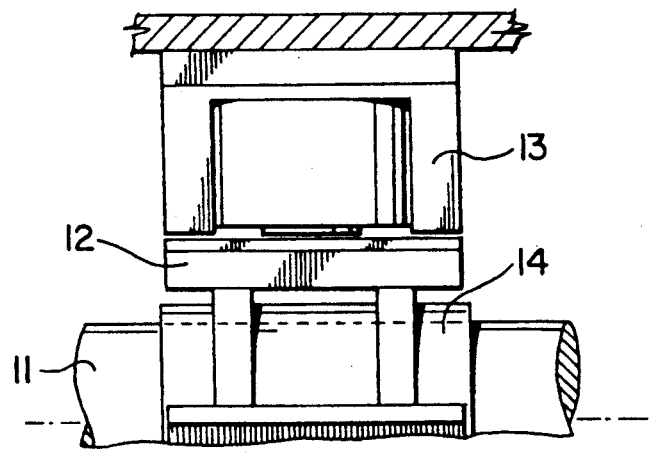
FIG. 8 is a partial side view of FIG. 7.

The resonant bar 11 is elastically mounted within the housing 20, as illustrated in FIG. IA, at the node points illustrated diagrammatically in FIG. IB where there is substantially zero vibration amplitude of the resonant bar 11. It is advantageous to mount the resonant bar 11 to the housing 20 at these points since, with such a mounting, relatively little power is lost through the nodal support positioner 23 and, since there is little or no movement of the resonant bar 11 at these node points when the resonant bar 11 is resonating, locating the resonant system, particularly the armatures 12, with respect to the electromagnetic excitation units 13 with the nodal support positioners 23 can be accomplished with good accuracy as illustrated in FIGS. 7 and 8.

As seen in FIG. 1B, four (4) points of maximum amplitude are illustrated. These points, shown at 24, 25, 30 and 31, are anti-nodes. Within the housing 20, the excitation unit armatures 12 are mounted to the resonant bar 11 through the isolation sleeves 14 and resilient elastomeric compound 21 at the highly stressed point or anti-node 30. A resilient mounting means 21 is not required at the anti-node 31 because the free end of the bar 11 is substantially non-stressed. The power transmission between both the excitation unit electromagnets 13 and the armatures 12, and the resonant bar 11 and the fluid medium 15 (FIG. 6A) in which the sonic generator 10 is mounted, is most efficient at the anti-nodes, since power is transferred both to the fluid medium 15 from the resonant bar 11, and to the resonant member 11 from the electromagnetic excitation units 13, in direct proportion to the amplitude of vibration of the resonant bar 11.

The use of the resilient elastomeric component and the sleeve 14 reduces stress concentrations applied to the resonant bar 11 caused by rigidly mounting, as by clamping or bolting or welding, the excitation unit armatures 12 directly to the bar. This is so because the free surface area of the elastomer 21 is quite small relative to the constrained surface area, which results in a layer which has very little compressibility. Thus, it will transmit substantially all of the force between the components of the resonant member 11, while at the same time the elastomer 21 allows the resonant bar 11 to freely flex in a substantially unrestrained configuration in its characteristic mode shape by absorbing the small relative deflections of the bar 11 caused by the flexure inherent in the characteristic mode shape.

While the elastomeric substance 21 used between the resonant bar 11 and the sleeve 14 is described as being urethane, it is clear that many other substances could be used with the appropriate operating characteristics including, as described, a resilient elastomeric component.

The sonic generator 10 has been described as being used in a fluid medium and it should be understood that such a fluid medium could be a liquid, a gas or a solid which has been fluidized by grinding to a finite particle size.

Figure 10:
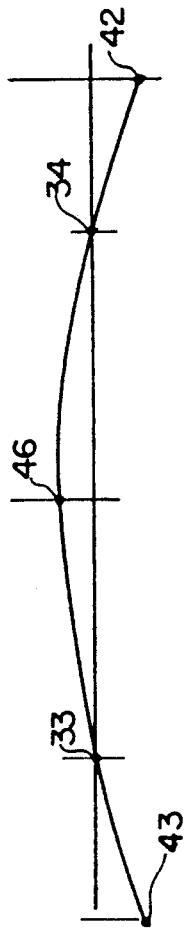
FIG. 10 is a diagrammatic view of the resonant member of FIG. 9 at the first resonant frequency.

Reference is now made to FIGS. 9 and 10 where the sonic generator 35 according to the invention is utilized in a grinding environment. A resonant member 32 is supported on nodal locations 33, 34 by airbags 36 (FIG. 9C) which can be inflated and placed at the nodal points 33, 34 of the resonant member 32, which nodal points have been calculated or have been found by simply resonating the resonant member 32 and observing the nodal locations. Super-Cushion Air Spring airbags manufactured by Goodyear have been found appropriate.

The electromagnetic drive units 40, 41 are connected to the resonant member 32 preferably at the anti-nodes 42, 43 (FIG. 9a) and are excited at the appropriate resonant frequency of the member 32. As previously described, the orientation of the excitation units causes a three dimensional, nutational vibration of the resonant member 32, which translates into a circular motion of the grinding chambers 44, 50 when viewed along the axis of the resonant member 32 which is important to grinding efficiency. The grinding chambers 44, 50 are mounted to the resonant member 32, preferably also at the anti-nodes 42, 43 by bolts 47. The grinding chambers 44, 50 and the drive units 40, 41 are rigidly connected to the resonant member 32 and for the purposes of determining the mode shape and resonance frequencies, become essentially a part of the resonant member 32.

The grinding chambers 44, 50 are filled with grinding media 45 such as steel, ceramic, cast iron, etc. The shape of the media 45 is arbitrary although balls or cylinders are preferable. The containers 44, 50 are filled with steel balls of an appropriate size, for example and the material to be ground will be fluidized in order to proceed through the media 45 in the grinding chambers 44, 50.

The material to be ground is fed into the grinding media 45 in the grinding chambers 44, 50 through ingress 52, and out the egress 51 of the grinding chambers 44, 50. Control of the material to be ground can be accomplished, for example, by pumping the fluidized material in to the grinding chambers 44, 50 at the desired rate.

For grinding a typical gold bearing ore, it is contemplated that the resonant member 32 will be a steel bar having a diameter of approximately 13 inches and a length of approximately 120 inches. With such dimensions, a natural frequency of the resonant member 32 would be approximately 120 Hz. The electromagnetic drive motors 40, 41 will have a power rating of approximately 75 Kw total and one will be mounted at each of the outer anti-nodes 42, 43. At the resonant frequency of 120 Hz, there will be three anti-nodes 43, 42, 46 and two nodes 33, 34 as seen in FIG. 10, one anti-node 46 being located at the centre of the resonant member 32.

It is contemplated that each of the grinding chambers 44, 50 would have a volume of approximately 15 litres with dimensions of approximately 8 in. diameter and about 18 in. length. Replaceable liners are also intended to be used for convenient replacement when the liners are worn. For gold, a grinding media such as steel, tungster carbide, zirconia, alumina, etc. could be used.

With the apparatus as contemplated and given above, there is intended to be size reduction from 1500 to 50 microns at a rate of 500 tonnes per day. It will be appreciated that these quantities are approximations only and that under actual operating conditions, they may change substantially.

Many modifications additional to those described will readily occur to those skilled in the art to which the invention relates and the specific embodiments described above should be taken as illustrative of the invention only and not as limiting its scope as defined in accordance with the accompanying claims.

What is claimed is:

1. A method of grinding material comprising supporting a member having at least one resonant frequency at nodal points such that said member is substantially unrestrained, rigidly and removably mounting at least one grinding chamber externally of and on a free end of said member, introducing grinding media into said grinding chamber, electromagnetically exciting said unrestrained member and said grinding chamber at a resonant frequency of said member thereby to commence the electromagnetic vibration of said grinding chamber and said grinding media within said chamber at said resonant frequency of said member, introducing material to be ground into said grinding chamber and removing said material following passage through said grinding media.

2. A method as in claim 1 wherein said member is electromagnetically excited with an electromagnet located at an anti-node of said member.

3. Grinding apparatus comprising an electromagnetically driven member having a plurality of nodes and anti-nodes at a resonant frequency, resilient mounting means located between a housing and said member at at least two nodes of said member, electromagnetic drive means for electromagnetically driving said member mounted to said member at at least one anti-node and at least one grinding chamber excitable by said electromagnetically driven member at said resonant frequency of said member, said chamber being externally, rigidly and removably mounted to a free end of said member.

4. Apparatus as in claim 3 and further comprising means to allow material to be ground ingress to and egress from said grinding chamber.

5. Apparatus as in claim 4 wherein said grinding chamber is rigidly connected to said member.

6. Apparatus as in claim 4 wherein said member is free to vibrate in the natural mode shape of the member without substantial constraint.

7. Apparatus as in claim 6 wherein said vibration supplied to said grinding chamber is substantially circular.

8. Apparatus as in claim 3 wherein said resilient mounting means includes air bags.

9. Apparatus as in claim 3 and further comprising replaceable liners within said grinding chamber.

* * * * *